United States Patent
Persuitti et al.

[11] Patent Number: 6,044,302
[45] Date of Patent: Mar. 28, 2000

[54] APPARATUS FOR CONNECTING A LEFT VENTRICULAR ACCESS LEAD TO A CARDIAC RHYTHM MANAGEMENT DEVICE

[75] Inventors: Kevin J. Persuitti, Andover; Greg L. Sundberg, Stillwater; Jeffrey T. Bartig, Maplewood; Mary L. Cole, St. Paul, all of Minn.

[73] Assignee: Cardiac Pacemakers, Inc., St. Paul, Minn.

[21] Appl. No.: 09/227,136

[22] Filed: Jan. 7, 1999

[51] Int. Cl.[7] .................................................. A61N 1/375
[52] U.S. Cl. ............................................. 607/37; 439/909
[58] Field of Search ................................ 607/36–38, 4, 607/122, 63, 119; 600/374; 439/909

[56] References Cited

U.S. PATENT DOCUMENTS

| | | | |
|---|---|---|---|
| 4,144,891 | 3/1979 | Lysfjord et al. | 607/37 |
| 5,374,279 | 12/1994 | Duffin, Jr. et al. | 607/37 |
| 5,679,026 | 10/1997 | Fain et al. | 607/37 |
| 5,935,160 | 8/1999 | Auricchio et al. | 607/122 |

OTHER PUBLICATIONS

International Standard, ISO 5841–3 and ISO 11318; ; Cardiac pacemakers—Part 3; First edition 1992–12–01.

Primary Examiner—Kennedy J. Schaetzle
Attorney, Agent, or Firm—Nikolai, Mersereau & Dietz, P.A.

[57] ABSTRACT

A multiport header for a cardiac rhythm management device includes at least one standard port and a separate port for a left ventricular access lead. The left ventricular access lead can only be electrically and mechanically coupled to the proper port. Standard leads cannot be electrically or mechanically coupled to the port for the left ventricular access lead.

9 Claims, 6 Drawing Sheets

APPARATUS FOR CONNECTING A LEFT VENTRICULAR ACCESS LEAD TO A CARDIAC RHYTHM MANAGEMENT DEVICE

BACKGROUND OF THE INVENTION

I. Field of the Invention

The present invention relates to implantable devices used to stimulate the heart to control the heart's rhythm. This invention is more specifically directed toward the connection between a cardiac rhythm management device such as an implantable pacemaker or defibrillator and a lead adapted to be implanted in the coronary veins on the left side of the heart.

II. Description of the Prior Art

As set forth in U.S. Pat. No. 5,803,928 granted on Sep. 8, 1998 to Tockman et al, important health advantages are achieved by positioning an electrode in a branch of the great vein of the heart for the purpose of stimulating the left ventricle. Such an electrode can, for example, be used to treat tachycardia. Such an electrode can also be used to treat heart failure.

Traditional leads are not designed to be implanted in the great vein. The leads, themselves, tend to be too big and inflexible to be advanced through the coronary sinus and into the great vein of the heart. These size and flexibility problems are compounded if one would try to implant the lead in this area using traditional stylets, guidewires and guide catheters given the size and flexibility of such equipment. To successfully implant the lead in the vasculature of the left side of the heart, both the lead and the equipment used to implant the lead should be smaller in diameter.

Successful treatment of tachycardia or heart failure can often best be achieved by stimulating different areas of the heart in a controlled and precisely timed manner. Thus, most cardiac rhythm management devices have a plurality of ports to which leads can be attached. Over the years, the port arrangement and the manner in which the leads are attached to the port have become standardized. Several significant problems exist, however, if this standard arrangement is used to secure a left-sided access lead to a cardiac rhythm management device.

For example, a guide catheter small enough to be useful in positioning the lead cannot be used with a lead having a standard connector arrangement because the connector arrangement of the lead is too large to permit the guide catheter to be removed. Also, if a standard connector arrangement is used, the left-sided lead could be mistakenly secured to the wrong port resulting in the improper delivery of pulses to the heart.

SUMMARY OF THE INVENTION

The present invention provides a solution to the various problems outlined above. Specifically, the header of the cardiac rhythm management device includes a specially designed port which can only accommodate the specially designed connector arrangement of a left ventricular access lead. The port includes all the seals required to prevent current leakage and the ingress of body fluids past the lead and into the port. Also, the lead is designed so that it can neither be captured nor damaged by the set screws of a standard port such as a port constructed in accordance with the IS-1 or DF-1 standards established by the International organization for Standardization.

DETAILED DESCRIPTION OF THE PREFERRED EMBODIMENTS

Cardiac rhythm management systems typically include a device such as a pacemaker or defibrillator and a plurality of leads. The device typically includes a metal can 2 which holds the electronics and a source of power, such as a battery. This can 2 may also serve as an electrode. Almost invariably, a header 10 is secured to the can 2. The header 10 is used to attach the leads to the electronics held by the can.

Figure 1:
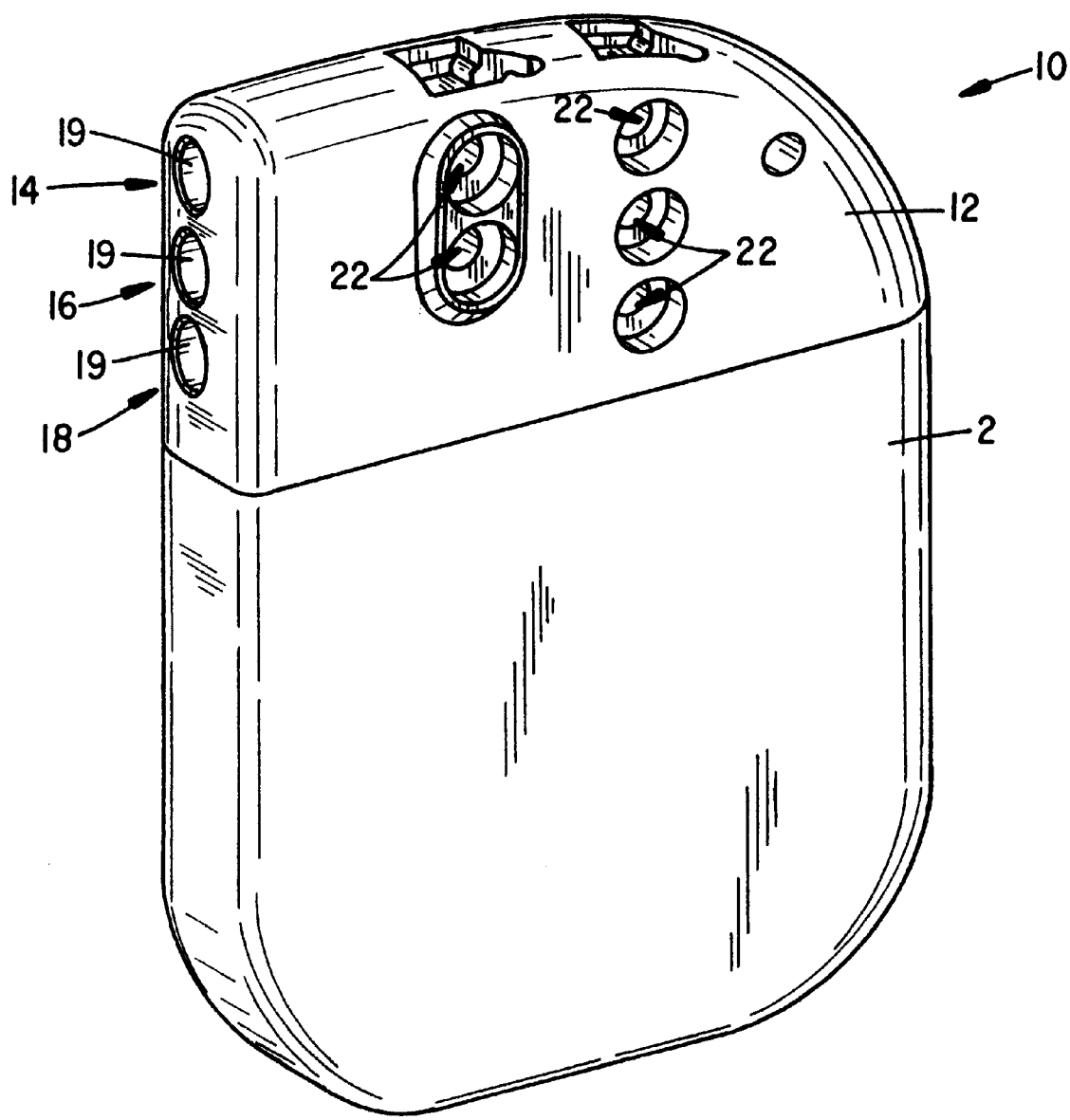
FIG. 1 is a perspective view of a header of a cardiac rhythm management device.

FIG. 1 shows a header 10. The header 10 has a body 12. The body 12 of header 10 includes a plurality of ports. FIG. 1 shows ports 14, 16 and 18. Ports 14 and 16 are of a standard configuration. More specifically, they are both constructed in accordance with Standard ISO 5841-3:1992 (E) of the International Organization for Standards and are hereinafter referred to as IS-1 ports. Port 18 is specially designed to receive a left ventricular access lead.

Figure 3:
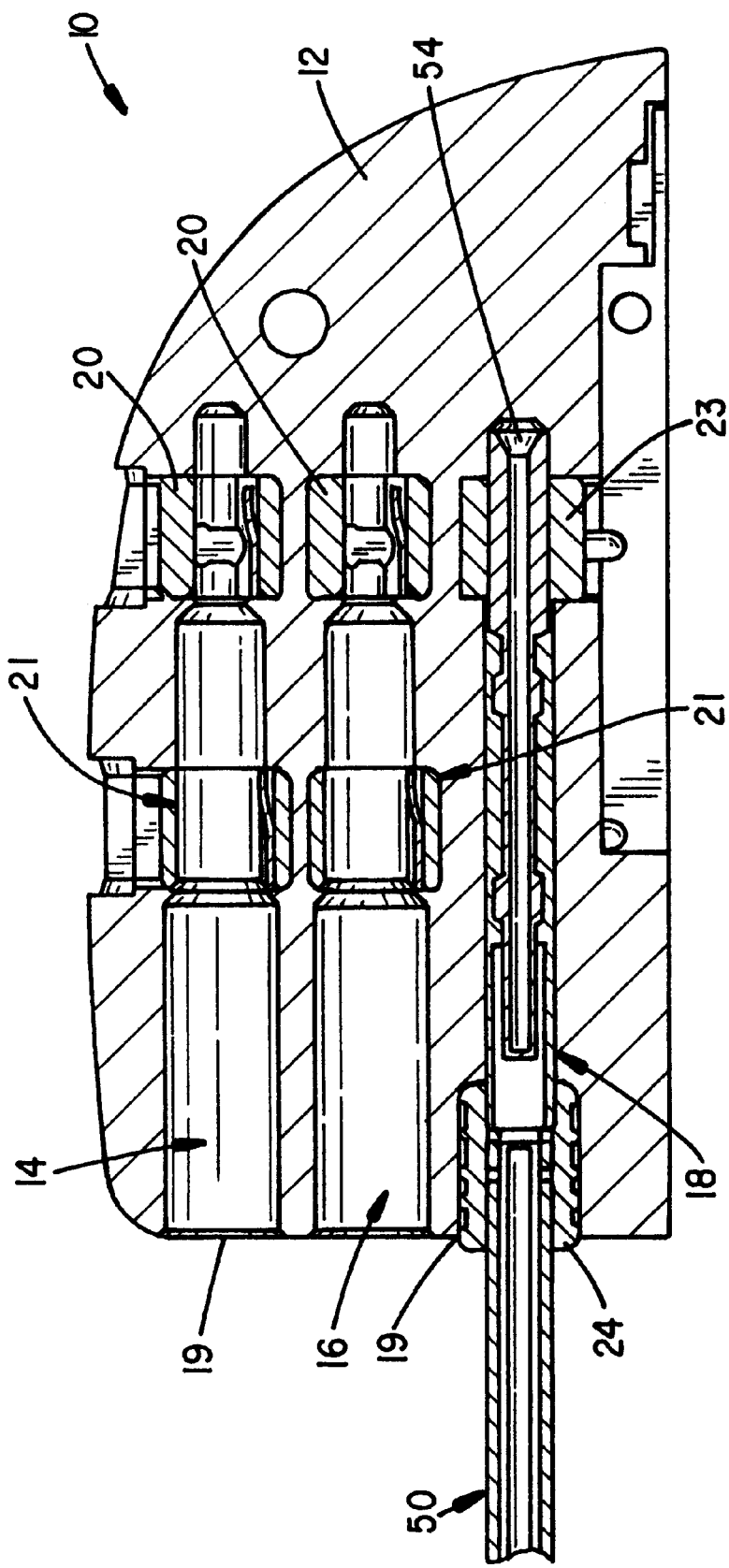
FIG. 3 is a cross-sectional view of the header shown in FIG. 1 with a left-sided access lead captured within a port designed for that lead.

Each port in the header 10 includes an orifice 19 and at least one metal connector block 20, 21 and 23 which includes a set screw 22 for engaging a lead to lock the lead in the port. The connector block 20, 21 and 23 and set screw 22 cooperate to mechanically and electrically couple the lead to the port of the header 10. Port 18 also includes an elastomeric seal 24. The elastomer seal 24 includes an outer sleeve 26 and a pair of sealing rings 28 and 30. As shown in FIG. 3, the entrance diameter of ports 14 and 16 are substantially larger than the diameter of port 18.

Figure 2:
FIG. 2 is a side view of the connector portion of a left ventricular access lead.

FIG. 2 shows the connector portion of the left ventricular access lead 50. The lead 50 includes a lead body 52 and a lead tip 54. The lead body 52 has an outer covering 56 made of an insulative material such as silicone rubber. The tip 54 is exposed and made of a conductive material such as titanium. The lead body 52 is sized so that it cooperates with the sealing rings 28 and 30 of the elastomeric seal 24 to prevent fluids from entering the header 10 through the orifice 18 and to prevent current leakage. As shown in FIG. 3, the tip 54 can enter the header's connector block 23 and be locked in place by the set screw 22 to form a suitable physical and electrical connection between the lead 50 and the header 10.

Figure 6:
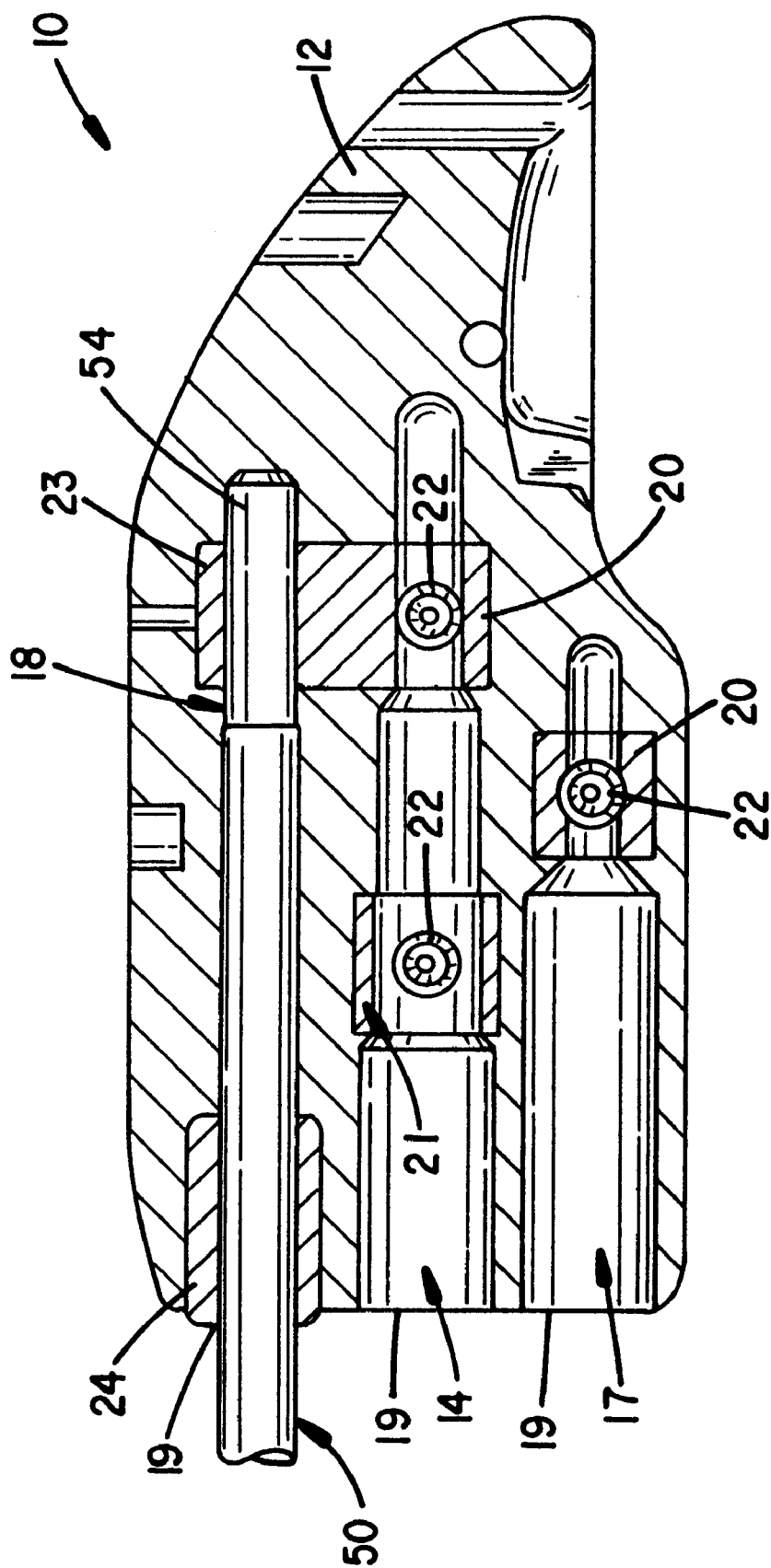
FIG. 6 is a cross-sectional view of an alternative header arrangement.

The alternative header arrangement shown in FIG. 6 also incorporates three ports numbered 14, 17 and 18. In FIG. 6, the port 18 is again designed to receive a left ventricular access lead. Port 14 is again a standard IS-1 port. In this embodiment port 17 is a port made in accordance with standard 11318:1993(E) of the organization for Standardization and is referred to as a DF-1 port. Thus, in this embodiment, the port 14 is designed to receive a pacing lead and port 17 is designed to receive a defibrillation lead. Again, the port 18 is designed so that neither a standard pacing lead nor a standard defibrillation lead can be coupled to the port 18. Likewise, a left ventricular lead cannot be coupled to either the IS-1 or DF-1 ports. Finally, given the differences outlined in the 5841-3:1992(E) and 11318:1993 (E) standards (which are incorporated by reference) leads made in accordance with one of those standards cannot be coupled to a port made in accordance with the other of said standards.

Figure 4:
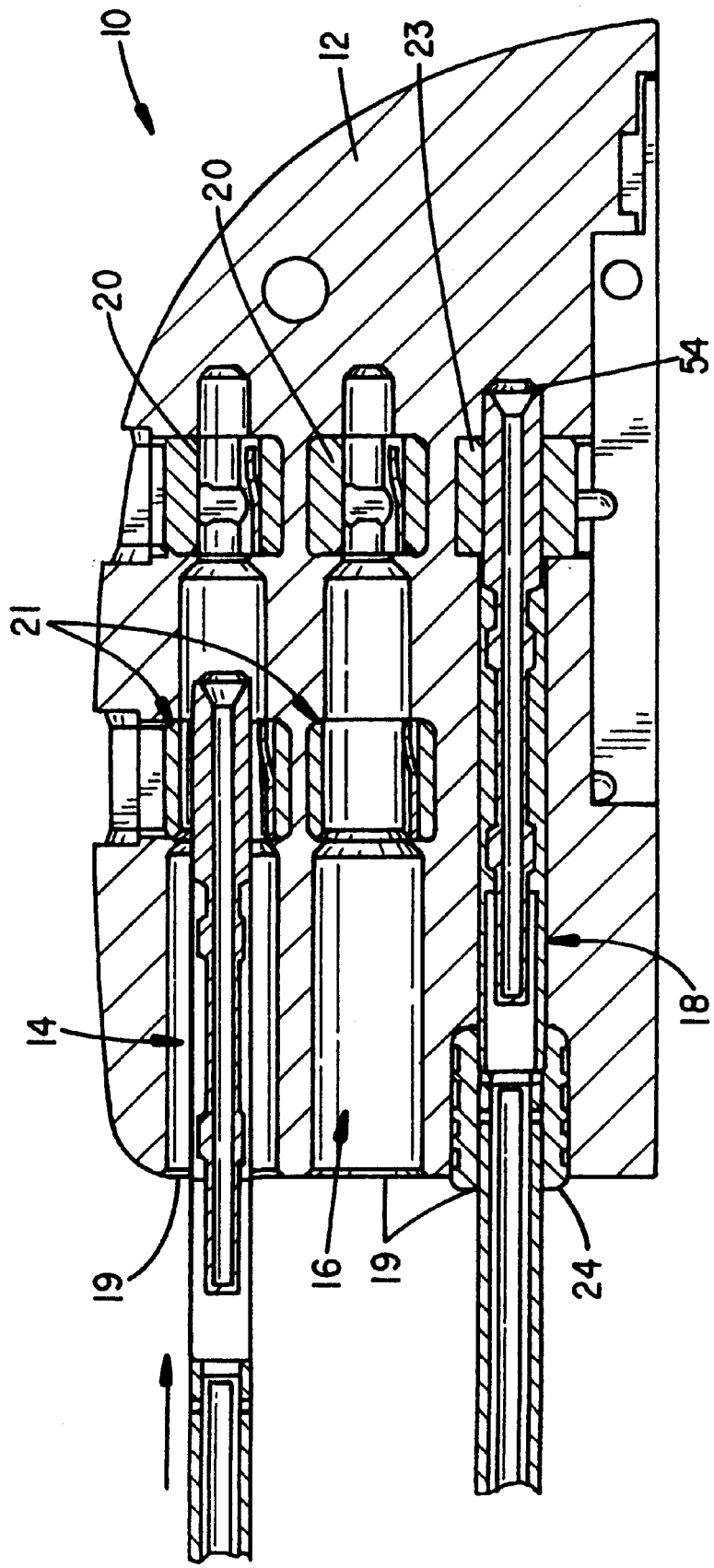
FIG. 4 is a cross-sectional view of the header shown in FIG. 1 with a left-sided access lead positioned in a standard port which is a part of the header.
Figure 5:
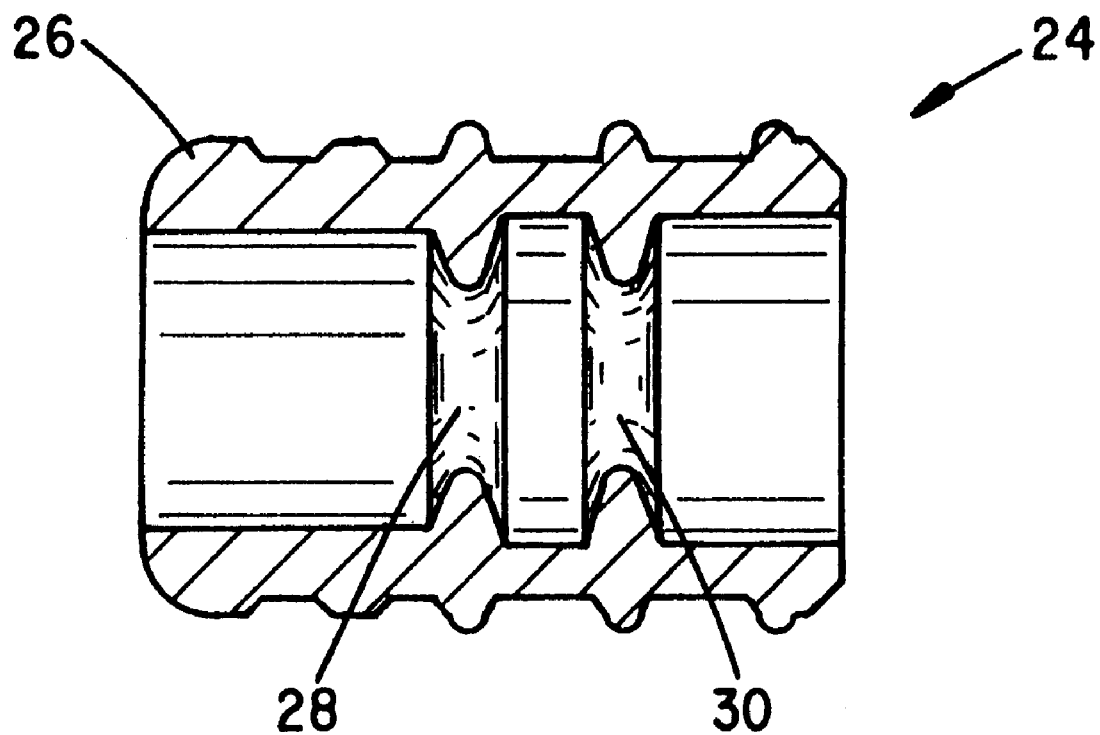
FIG. 5 is a cross-sectional view of a seal used in conjunction with the port for the left ventricular access lead.

Several advantages are derived from the arrangements described above. First, a standard lead tip made in accordance with IS-1 standards can be inserted into and coupled to either port 14 or port 16 in FIG. 3 or to port 14 in FIG. 6. Further, a standard DF-1 lead can be coupled to port 17 in FIG. 6. However, the diameter of port 18 is sufficiently smaller than the diameter of either a standard IS-1 or DF-1 lead making it impossible to insert a standard IS-1 or DF-1 lead into and have it captured by port 18. Second, the diameter of the body 52 of left ventricular access lead 50 is substantially smaller than that of a standard lead. While it is possible to insert the left ventricular access lead into either ports 14, 16 or 17 as shown at FIGS. 4 and 6, it will not be captured by connector block 21 because it is not possible to turn the set screw down far enough to capture the lead tip or even engage the lead body. Thread stops of connector block 21 are provided to limit the travel of the set screws 22 associated with ports 14 and 16 to ensure that the left ventricular access lead 50 cannot be captured by these ports. Third, tip 54 of the left ventricular access lead 50 has a diameter too large to permit the tip 54 to be inserted into the metal connector block 20 of either port 14, 16 or 17. Thus, the surgeon will immediately know the lead 50 has been inserted into the incorrect port and there is no way to fix the lead 50 in place in the wrong port. Fourth, standard IS-1 and DF-1 leads typically have sealing rings projecting outwardly from the lead body. Using a separate seal 24 instead makes it easier to slide a small diameter guide catheter over the end of the lead. Hence, one can use smaller diameter guide catheters to implant the lead 50.

What is claimed is:

1. For use in conjunction with cardiac leads, a header for a cardiac rhythm management device incorporating a plurality of ports, each port including an orifice and means for electrically and mechanically coupling a cardiac lead to said cardiac rhythm management device, the diameter of the orifice of a first of said ports being smaller than the diameter of the orifice of the second of said ports and the means for electrically and mechanically coupling a lead to a second of said ports being incapable of engaging a lead having a diameter small enough to be received by said first port.

2. The apparatus of claim 1 wherein said first port incorporates a seal comprising a tubular sleeve and a pair of sealing rings projecting inwardly from said tubular sleeve, said pair of sealing rings sized to cooperate with a cardiac lead coupled to said first port to prevent fluids from entering the orifice and to prevent current leakage.

3. The apparatus of claim 1 wherein the diameter of the orifice of the first of said ports is too small to receive a cardiac lead of a size capable of being coupled by said second port's means for electrically and mechanically coupling a lead to the port.

4. The apparatus of claim 1 wherein said means for electrically and mechanically coupling a cardiac lead to the second of said ports includes a set screw and a thread stop for restricting the movement of the set screw past a predetermined point.

5. An apparatus for providing electrical stimulation to the heart, said apparatus comprising:

(a) a cardiac rhythm management device having a header, said header having a plurality of ports, each port including an orifice and at least one connector block having a channel and a set screw for coupling a cardiac lead to said cardiac rhythm management device, the orifice of one of said ports being smaller than the orifice of a second of said ports, the channel of the connector block of said one of said ports being larger than the channel of the connector block of said second of said ports;

(b) a first cardiac lead having a first body and a first tip, said first body and first tip being sized to permit the first cardiac lead to be coupled to said one of said ports, but said tip and body being sized to prevent said lead from being coupled to or damaged by said second of said ports; and (c) a second cardiac lead having a second body and a second tip, said second body and said second tip being sized to permit the second cardiac lead to be coupled to said second of said ports and said second lead body being too large to enter the orifice of said first of said ports.

6. For use in conjunction with cardiac leads, a header for a cardiac rhythm management device incorporating a first port and at least two IS-1 ports, each port including an orifice and means for electrically and mechanically coupling a cardiac lead to said cardiac rhythm management device, the diameter of the orifice of said first port being smaller than the orifice of said IS-1 ports and the means for electrically and mechanically coupling a lead to said IS-1 ports being incapable of engaging a lead having a diameter small enough to be received by said first port.

7. An apparatus for providing electrical stimulation to the heart, said apparatus comprising:

(a) a cardiac rhythm management device having a header, said header having a first port and two IS-1 ports, each port including an orifice and at least one connector block having a channel and a set screw for coupling a cardiac lead to said cardiac rhythm management device, the orifice of the first port being smaller than the orifice of a said IS-1 ports, the channel of the connector block of said first port being larger than the channel of the connector block of said IS-1 ports;

(b) a first cardiac lead having a first body and a first tip, said body and first tip being sized to permit the first cardiac lead to be coupled to said first port, but said tip and body being sized to prevent said lead being coupled to or damage by said IS-1 ports; and (c) a pair of said cardiac leads each having a second body and a second tip, said second body and said second tip being sized to permit said pair of second cardiac leads to be coupled to said IS-1 ports and each of said second-lead bodies being too large to enter the orifice of said first of said ports.

8. For use in conjunction with cardiac leads, a header for a cardiac rhythm management device incorporating a first port, an IS-1 port and a DF-1 port, each of said ports including an orifice and means for electrically and mechanically coupling a cardiac lead to said cardiac rhythm management device, the diameter of the orifice of said first port being smaller than the diameter of the orifice of the IS-1 port and the diameter of the orifice of the DF-1 port and the means for electrically and mechanically coupling a lead to the IS-1 and DF-1 ports being incapable of engaging a lead having a diameter small enough to be received by said first port.

9. An apparatus for providing electrical stimulation to the heart, said apparatus comprising:

(a) a cardiac rhythm management device having a header, said header having a first port, an IS-1 and a DF-1 port, each of said ports having an orifice and at least one connector block having a channel and a set screw for coupling a cardiac lead to said cardiac rhythm management device, the orifice of said first port being smaller than the orifice of the IS-1 and DF-1 ports, the channel of the connector block of said first port being larger than the channel of the connector block of said IS-1 and DF-1 ports;

(b) a first cardiac lead having a first body and a first tip, said first body and said first tip being sized to permit the first cardiac lead to be coupled to said first port, but said tip and body being sized to prevent said lead from being coupled to or damaged by said IS-1 or DF-1 ports;

(c) a second cardiac lead having a second body and a second tip, said second body and said second tip being sized to permit the second cardiac lead to be coupled to said IS-1 port and said second lead body being too large to enter the orifice of said first port; and (d) a third cardiac lead having a third body and a third tip, said third body and said third tip being sized to permit the third cardiac lead to be coupled to said DF-1 port and said third lead body being too large to enter the orifice of said first of said ports.

* * * * *

UNITED STATES PATENT AND TRADEMARK OFFICE
CERTIFICATE OF CORRECTION

PATENT NO. : 6,044,302
DATED : March 28, 2000
INVENTOR(S) : Kevin J. Persuitti, et al It is certified that error appears in the above-indentified patent and that said Letters Patent is hereby corrected as shown below:

Column 3, claim 1, line 44, delete "the", first occurrence, and insert -- an --; line 45, delete "a", second occurrence, and insert -- the --.

Column 4, claim 7(c), line 50, delete "said".

Signed and Sealed this

Thirteenth Day of February, 2001

Attest:

NICHOLAS P. GODICI

Attesting Officer

Acting Director of the United States Patent and Trademark Office